United States Patent
Leong et al.

(10) Patent No.: US 11,311,629 B2
(45) Date of Patent: Apr. 26, 2022

(54) DNA-TEMPLATED MICELLE AND USES THEREOF

(71) Applicant: THE TRUSTEES OF COLUMBIA UNIVERSITY IN THE CITY OF NEW YORK, New York, NY (US)

(72) Inventors: Kam W. Leong, New York, NY (US); Yeh-Hsing Lao, New York, NY (US); Tzu-Chieh Ho, New York, NY (US); Smruthi Suryaprakash, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 128 days.

(21) Appl. No.: 16/492,320

(22) PCT Filed: Feb. 27, 2018

(86) PCT No.: PCT/US2018/019926
§ 371 (c)(1),
(2) Date: Sep. 9, 2019

(87) PCT Pub. No.: WO2018/164883
PCT Pub. Date: Sep. 13, 2018

(65) Prior Publication Data
US 2021/0128746 A1 May 6, 2021

Related U.S. Application Data

(60) Provisional application No. 62/469,494, filed on Mar. 9, 2017.

(51) Int. Cl.
*A61K 47/69* (2017.01)
*A61K 47/55* (2017.01)
(Continued)

(52) U.S. Cl.
CPC ........ *A61K 47/6907* (2017.08); *A61K 31/136* (2013.01); *A61K 31/4178* (2013.01);
(Continued)

(58) Field of Classification Search
CPC .................................................. A61K 47/6907
See application file for complete search history.

(56) References Cited

PUBLICATIONS

Zhou, J. et al., "Cell-type-specific, Aptamer-functionalized Agents for Targeted Disease Therapy", Molecular Therapy Nucleic Acids, Jun. 17, 2014, vol. 3, No. e169; pp. 1-17.
(Continued)

*Primary Examiner* — Benjamin J Packard
(74) *Attorney, Agent, or Firm* — Nath, Goldberg & Meyer; Joshua B. Goldberg; Scott H. Blackman (57) ABSTRACT

The present invention discloses a multifunctional DNA-templated micelle system that has a payload carrier of at least a DNA bridge and a functionalized polyethylene glycol (PEG) segment. The micelle can be used to deliver molecules, such as drugs and polynucleotides, to targeted cells for pharmaceutical uses. The PEG segment provides a functional group, such as amine, for ligand conjugation. The DNA-templated micelle of the present invention is highly controllable in size, loading efficiency and tissue targeting, and can carry multiple payloads for targeted combination strategies in cancer therapy, such as gene delivery, gene therapy, and immunotherapy.

15 Claims, 8 Drawing Sheets

(51) Int. Cl.

| | | |
|---|---|---|
| *A61K 47/64* | (2017.01) | |
| *A61K 47/68* | (2017.01) | |
| *A61K 47/54* | (2017.01) | |
| *A61K 47/60* | (2017.01) | |
| *A61P 35/02* | (2006.01) | |
| *A61K 31/136* | (2006.01) | |
| *A61K 31/4178* | (2006.01) | |
| *A61K 31/7105* | (2006.01) | |
| *A61K 38/46* | (2006.01) | |
| *A61K 48/00* | (2006.01) | |
| *C12N 15/88* | (2006.01) | |

(52) U.S. Cl.
CPC ........ *A61K 31/7105* (2013.01); *A61K 38/465* (2013.01); *A61K 47/549* (2017.08); *A61K 47/551* (2017.08); *A61K 47/60* (2017.08); *A61K 47/64* (2017.08); *A61K 47/6845* (2017.08); *A61K 47/6901* (2017.08); *A61K 48/0041* (2013.01); *A61P 35/02* (2018.01); *C12N 15/88* (2013.01)

(56) References Cited

PUBLICATIONS

Elais, D.R. et al., "Effect of ligand density, receptor density, and nanoparticle size on cell targeting", Nanomedicine, Feb. 2013, Epub Jun. 9, 2012, vol. 9, No. 2; pp. 194-201.

Makino, A. et al., "Size control of cord-shell-type polymeric micelle with a nonometer precision", Langmuir, Jan. 21, 2014, Epub Jan. 8, 2014, vol. 30, No. 2; pp. 669-674.

May, M., "Gene Transfer: Taming Diversity", Science, Jun. 18, 2009, vol. 324, No. 5934; p. 1587; p. 2, 7th & 8th paragraphs.

International Search Report and Written Opinion of PCT/US/19926 dated May 7, 2018, with forms ISA-220-210-237.

FIGURE 1.

Payload Carrier

*Payload type:* drug or nucleic acid
*Ligand type:* small compound, peptide, Ab or aptamer

Panel A

Panel B

DNA-TEMPLATED MICELLE AND USES THEREOF

FIELD OF THE INVENTION

The present invention discloses a multifunctional DNA-templated micelle system which comprises a payload carrier comprising at least a DNA bridge and a functionalized polyethylene glycol (PEG) segment. The DNA-templated micelle system can be used to deliver various molecules, such as, compounds, drugs, or polynucleotides, for pharmaceutical uses.

BACKGROUND OF THE INVENTION

Nanoparticles have been utilized for clinical applications as drug carriers. The development of nano-medicines for the treatment of cancer has been done to enhance drug efficacy or to reduce adverse drug effects by targeted delivery locally, such as the delivery of chemotherapeutic drugs to the tumor site. Nano-medicines provide the advantages of increasing the therapeutic efficacy of anti-cancer drugs with less delivery barriers. A wide range of organic and inorganic nanoparticles with dimensions of less than several hundred nanometers have been used for cancer therapy for tumor targeting.

The limitation of effectiveness of cancer treatment is the high toxicity of anti-cancer agents and the lack of selective delivery of drugs to the tumor site. Nano-medicines utilizing nano-carriers loaded with drugs are promising in cancer treatment due to their unique physico-chemical characteristics, such as increasing solubility and stability for targeted delivery, and improving distribution of anti-cancer drugs while decreasing drug resistance of tumors. In addition, nanoparticles can provide enhanced permeability and retention effect that allows for accumulation of therapeutics in tumors at a much higher concentration than that in healthy cells, which reduces the systemic toxicity of anti-cancer drugs.

Some nano-medicines for cancer therapy are effective in terms of improved bioavailability and tolerability, but there is a need to increase drug performance, such as to improve the capacity of drug carriers to deliver high doses of anti-cancer drugs to specific locations in the body. Some stimuli responsive carriers have been developed to release drugs through internal or external stimuli, such as liposomes, polymeric micelles, nanogels and mesoporous silica nanoparticles. (van Elk et al., Nanomedicines for advanced cancer treatments: Transitioning towards responsive system, Int J Pharm. 2016 October; 515(1-2): pp. 132-164)

Several multifunctional nano-carrier systems have been published. Kataoka et al. (US 2016/0184457 A1, Nucleic acid-encapsulating polymer micelle complex and method for producing the same) discloses a nucleic acid encapsulating polymer micelle complex comprising a block polymer containing an uncharged hydrophilic polymer chain block, a cationic polymer chain block, and double-stranded or single-stranded DNAs. Haag et al. (U.S. Pat. No. 9,102,595 B2, Compounds suited as nanocarriers for active agents and their use) discloses a compound suited as a nano-carrier for active agents comprising a polyglycerol core with an amine-containing residue, and further recites a nano-carrier system comprising a nucleic acid or pharmacologically active small molecules to be carried by and bound to said nano-carrier in a covalent, ionic or complexed manner. Mohapatra et al. (US 2013/0243867 A1, Micelle compositions and methods for their use) discloses a micelle composition comprising a micelle containing polyethylene glycol-phosphatidyl ethanolamine (PEG-PE), a DC-cholesterol and a dioleoylphosphatidyl-ethanolamine (DOPE) coated with either or both of a pharmaceutical compound core and a polynucleotide coating.

For cancer therapy, single drug treatment may not be sufficient to completely eliminate cancer cells at least partially due to their heterogeneity and insensitivity against the induced inhibitory signals. There are needs to develop nano-medicines to improve the therapeutic strategies against cancer to obtain sophisticated targeting strategies with multi-functionalities for synergistic cancer therapies, such as co-delivering multiple anti-cancer drugs and DNA in a controlled manner with improved pharmacokinetic profile, pharmacodynamics profile, chemical stability, solubility, controlled release, and bio-distribution of anti-cancer drugs. In addition, there remain concerns over potential toxicity of nano-particles, high heterogeneity of nanoparticles (high polydispersity) in different batches, loss of drug efficacy during encapsulation and delivery, and limitations of the scalability of nano-medicines. The present invention now addresses these needs and provides viable improvements that have not been previously disclosed in the art.

SUMMARY OF THE INVENTION

The present invention now provides a multifunctional DNA-templated micelle system comprising a payload carrier which comprises at least a DNA bridge and a functionalized polyethylene glycol (PEG) segment. The micelle system can be used to deliver molecules, such as drugs and polynucleotides, to targeted cells for pharmaceutical uses and benefits. The DNA-templated micelle system can also be used as a stabilizer of nanoparticle formation.

The present invention provides a micelle system for delivering at least one payload to cells, the micelle system comprising at least one payload carrier, wherein the payload carrier comprises at least one DNA bridge and at least one functionalized PEG segment, wherein the functionalized PEG segment is covalently bound to the DNA bridge, wherein the DNA bridge can carry at least one payload through intercalation or nucleotide base pairing.

The functionalized PEG segment of the micelle system of the present invention can further conjugated to at least one ligand with a controllable ligand density in the range of from 0% to 100%. The payload carrier of the micelle system can be preloaded with at least one payload prior to the formation of micelle and can be further conjugated with at least one ligand prior to the formation of micelle. The functionalized PEG segment of the payload carrier can be an amine-functionalized PEG segment with the molecular weight in the range of from 1 kD to 30 kD. The DNA bridge of the payload carrier can be a single-stranded DNA in the range of from 8 nucleotides to 100 nucleotides.

The payload of the micelle system of the present invention may be selected from the group that includes small molecules, compounds, drugs, chemodrugs, polynucleotides, DNA, genes, messenger RNA (mRNA), aptamers, and combinations thereof. The ligand of micelle system of the present invention is different from the payload and may be selected from the group that includes of small molecules, peptide, antibodies, aptamers, polynucleotides, and combinations thereof. The size of the micelle of the present invention is from about 5 nm to about 250 mm with the polydispersity of less than 0.1.

In one aspect, the present invention provides a method for delivering a payload to cells of a subject for disease treatment, comprising administering to the subject a pharmaceutical composition comprising the micelle system of the present invention, including the disease treatments of cell transfections, gene therapy, chemotherapy, immunotherapy, cancer treatment, disease monitoring, brain tumor chemotherapy, glioblastoma chemotherapy, or leukemia immunotherapy.

In yet another aspect, the present invention provides a kit for performing a cell transfection reaction, which comprises the micelle system of the present invention.

The details of the preferred embodiments of the present invention are set forth in the accompanying figures and detailed description herein. Once these details of the invention are known, numerous additional innovations and changes will become obvious and implementable to one of ordinary skill in the art.

BRIEF DESCRIPTION OF THE FIGURES

Further features of the inventive concept, its nature and various advantages will be more apparent from the following detailed description, taken in conjunction with the accompanying figures.

DETAILED DESCRIPTION OF THE INVENTION

Throughout this description, the preferred embodiments and examples provided herein should be considered as exemplar, rather than as limitations of the present invention.

The present invention discloses a multifunctional DNA-templated micelle system which can be used to deliver various components, such as small molecules, compounds, drugs, chemodrugs, polynucleotides, DNA, genes, messenger RNA (mRNA), aptamers or combinations thereof, to targeted cells or tumor sites for pharmaceutical uses, such as cell transfections, gene therapy, chemotherapy, immunotherapy, cancer treatment, disease monitoring, brain tumor chemotherapy, glioblastoma chemotherapy, or leukemia immunotherapy.

The present invention provides a micelle system for delivering at least one payload to cells, the micelle system comprising at least one payload carrier, wherein the payload carrier comprises at least one DNA bridge and at least one functionalized polyethylene glycol (PEG) segment, wherein the functionalized PEG segment is covalently bound to the DNA bridge, wherein the DNA bridge can carry at least one payload through intercalation or nucleotide base pairing.

Figure 1:
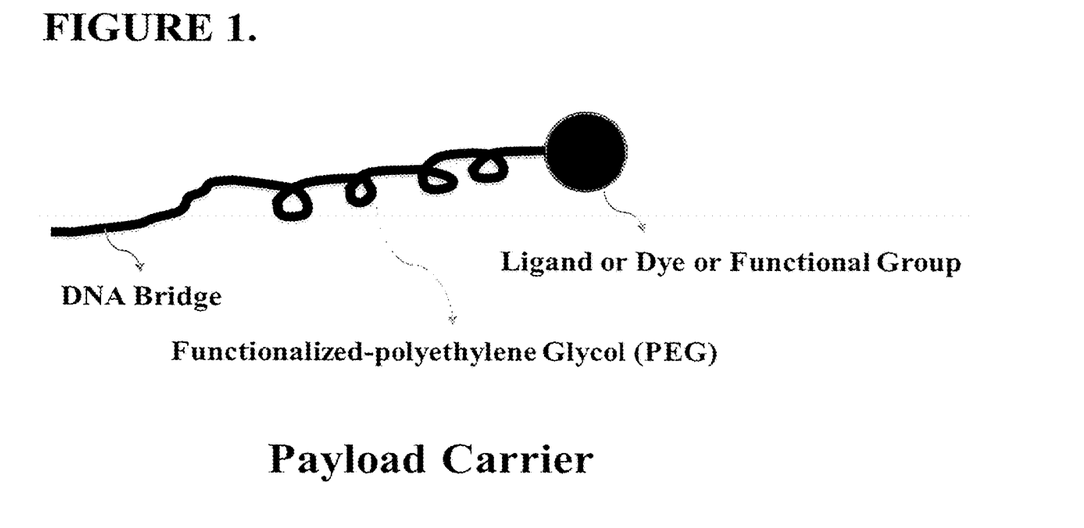
FIG. 1 shows a payload carrier comprising at least a DNA bridge and a functionalized-polyethylene glycol (PEG).
Figure 2:
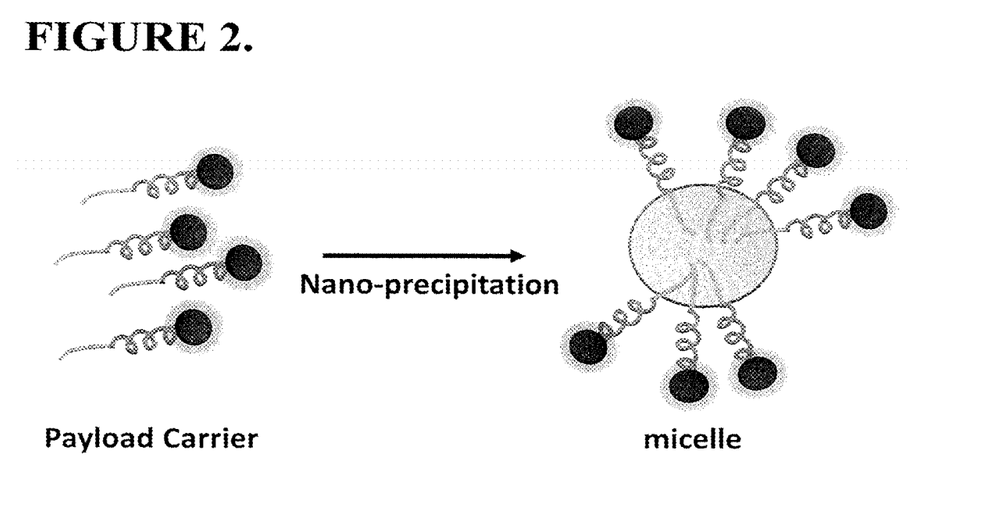
FIG. 2 shows the formation of a DNA-templated micelle through nano-precipitation. The micelles include a payload carrier comprising at least a DNA bridge and at least a functionalized-PEG.

The DNA-templated micelle system of the present invention includes a payload carrier which comprises at least a DNA bridge and a functionalized PEG segment (FIG. 1), such as an amine-functionalized PEG. The payload carrier of the present invention can be used to form DNA-templated micelles through nano-precipitation (FIG. 2). The formed DNA-templated micelle has low toxicity and are narrowly dispersed and colloidally stable. The DNA bridge of the payload carrier contains a single-stranded DNA and serves as a delivery vehicle for various payloads (such as small molecules, compounds, drugs, chemodrugs, polynucleotides, DNA, mRNA, aptamers, or combinations thereof), including delivering drugs through intercalation, or delivering polynucleotides through Watson-Crick nucleotide base pairing. For example, for loading a chemodrug through the DNA bridge of the payload carrier, a complementary single-stranded DNA fragment without further PEG is added to form a DNA-duplex with the DNA bridge, then the chemodrug can be loaded to the payload carrier through intercalation by inserting the chemodrug to the DNA duplex.

The functionalized PEG segment can be conjugated to at least one ligand, e.g. various ligands (such as small molecule, peptide, antibody, aptamer, polynucleotide, or combinations thereof) for tumor targeting. In one embodiment, the DNA bridge of the payload carrier is a single-stranded DNA with the size of in the range of from 8 to 100 nucleotides, preferred in the range of from 20 to 40 nucleotides, and the molecular weight of the PEG segment is in the range of from 1 kD to 30 kD, preferred in the range of from 2 kD to 20 kD.

Figure 3:
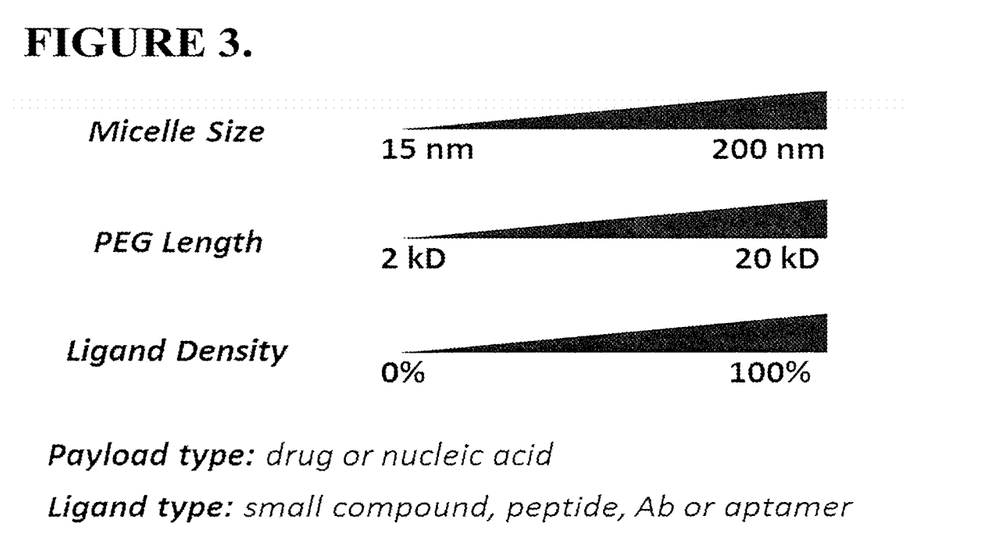
FIG. 3 shows the tunable ranges of micelle size, PEG length, and ligand density.

The DNA-templated micelle of the present invention is tunable with regards to size, ligand type, ligand density, and stability (FIG. 3), which is precisely controllable and provides the advantages of stability, specificity, and versatility. The payload carrier of the micelle may or may not be conjugated to a ligand. When the micelle is formed by mixing the payload carriers without ligand, the ligand density of this particular micelle is defined as 0% ligand density. When the micelle is formed by mixing the payload carriers which are all conjugated with ligands, the ligand density of this particular micelle is defined as 100% ligand density. The versatility of the DNA-templated micelle system of the present invention can be achieved by mixing payload carriers with or without conjugated ligands in a desired ratio, from 0% to 100% of ligand density, to form micelles with various ligand densities. Therefore, the ligand density of the DNA-templated micelle of the present invention is precisely controllable for the needs of designing various cancer therapy strategies.

Payloads and ligands can be preloaded separately before the formation of the DNA-templated micelles. The DNA-templated micelle is capable of carrying various payloads and ligands simultaneously to provide versatile strategies for cancer treatment for enhanced therapeutic index and outcome. The properties of the DNA bridge can be tuned precisely to fit the requirement of various applications, such as a partial complementary to a specific polynucleotide with a desirable melting temperature. Loading efficiency and ligand density of the multifunctional DNA-templated micelles are therefore controllable. The DNA-templated micelle of the present invention provides the advantages of simultaneously delivering multiple therapeutic payloads and ligands with high efficiency and low cytotoxicity to enhance the efficacy of cancer therapy.

The typical size of the DNA-templated micelles of the present invention ranges from 5 nm to 250 nm, preferred in the range of from 15 nm to 200 nm, depending on the sizes of the components in the micelles, such as the sizes of the DNA bridge, PEG, ligands, or loaded polynucleotides. In particular, the size of PEG-DNA and the presence of PEG are critical to control the formation of micelle in nano-sized. The polydispersity or heterogeneity of the DNA-templated micelles is typically lower than 0.1.

In one aspect, the present invention provides a system to transfect cells with polynucleotides, including mRNAs and small nucleic acids. Polynucleotides are loaded to the DNA bridge through Watson-Crick nucleotide base pairing. The loaded micelles can deliver polynucleotides to a wide spectrum of cell lines, including adherent cells and suspension cells, with 50-70% transfection efficiency and <10% cytotoxicity.

In one embodiment, the design of the payload carrier can contain a long PEG segment to reduce undesirable uptake by the normal cells, and the long PEG segment can be conjugated with a specific ligand targeting a unique type of tumor. Therefore, micelles containing such drug-loaded payload carriers can deliver drugs to and specifically kill tumors expressing the specific target of the ligand.

The present invention also provides a DNA-templated micelle for leukemia immunotherapy. As an example, two types of the payload carriers are designed. One type is conjugated with the antibody that recognizes a leukemic stem cell biomarker, and the other type is conjugated with human Fc protein to recruit immune cells. In addition, the payload carriers are loaded with drugs. Micelles containing such modified and loaded payload carrier can specifically kill cancer cells and also induce phagocytosis and antibody-dependent cell-mediated cytotoxicity of immune cells.

The DNA-templated micelle of the present invention can be used as a superior delivery vehicle for both drug and gene delivery. It can be a potential modality for cancer therapy as its properties are programmable and can be further customized to resolve the heterogeneous issues on cancer patients. In addition, the present invention provides a method for delivering a payload to cells of a subject for disease treatment. In yet another aspect, the present invention provides a kit for performing a cell transfection reaction, which comprises the micelle system of the present invention.

EXAMPLE

The following examples illustrate the benefits and advantages of the present invention. The applications of the multifunctional DNA-templated micelle are shown in the examples.

Example 1. Synthesis of Payload Carriers and the Formation of DNA-Templated Micelles The payload carrier comprised at least an amine-functionalized PEG segment and a DNA bridge (FIG. 1) was synthesized using Click chemistry and purified by reversed-phase high performance liquid chromatography (HPLC). Amine-PEG-azides were purchased from Nanocs Inc. (New York, N.Y.) or Laysan Bio, Inc. (Arab, AL). The single-stranded 5'-hexynyl-DNA was synthesized by IDT (Coralville, Iowa), and its molecular weight was confirmed by ESI-MS (electrospray ionization mass spectrometry). For Click chemistry, the reaction was carried out in 200 mM trithylamiimum buffer (pH 7) containing 50% DMSO (dimethyl sulfoxide) with single-stranded DNA (50 µM), amine-PEG-azide (250 µM), L-ascorbic acid (10 mM) and copper (II)-TBTA complex (500 µM) (TBTA is tris (benzyltriazolylmethyl)amine; copper(II)-TBTA is a catalyst used for Click Chemistry conjugation reaction) in an argon atmosphere for overnight at room temperature. The product was purified by reversed-phase HPLC and then lyophilized.

After the payload carrier was loaded with payloads (such as chemodrugs or polynucleotides) or was conjugated with ligands (such as small molecules, peptides, antibodies, aptamers, or nucleotides), the DNA-templated micelle was formed through nano-precipitation (FIG. 2). The micelle was formed by adding equal volume of the Tris buffer containing 250 mM calcium chloride and 0.1 mM EDTA (pH 7.6) to the loaded/modified payload carriers in a solution (50 mM HEPES buffer with 1.3 mM sodium phosphate and 140 mM sodium chloride, pH 7.1), then mixing for 1 min at room temperature.

The sizes of resulted DNA-templated micelles ranged from 15 nm to 200 nm. The resulted micelles had the polydispersity at lower than 0.1 and was stable in serum-containing environment, such as in complete cell culture medium.

Example 2. Preparation of a DNA Template Library

A DNA library was prepared for constructing the DNA bridge of the payload carrier. The payload carriers include various single-stranded DNA motifs (such as polyT, polyGC) with different melting temperatures (such as 37° C. or 52° C.). The payload carriers also comprise various PEG segments in the range of from 2 kD to 20 kD, such as in the size of 2 kD, 5 kD, 10 kD or 20 kD. The linkage between DNA and PEG was non-biodegradable or biodegradable with various termini, such as methylated, free amine, dye-conjugated or ligand-conjugated.

Example 3. The Influence of the Lengths of PEG and Single-Stranded DNA Motif

Figure 4:
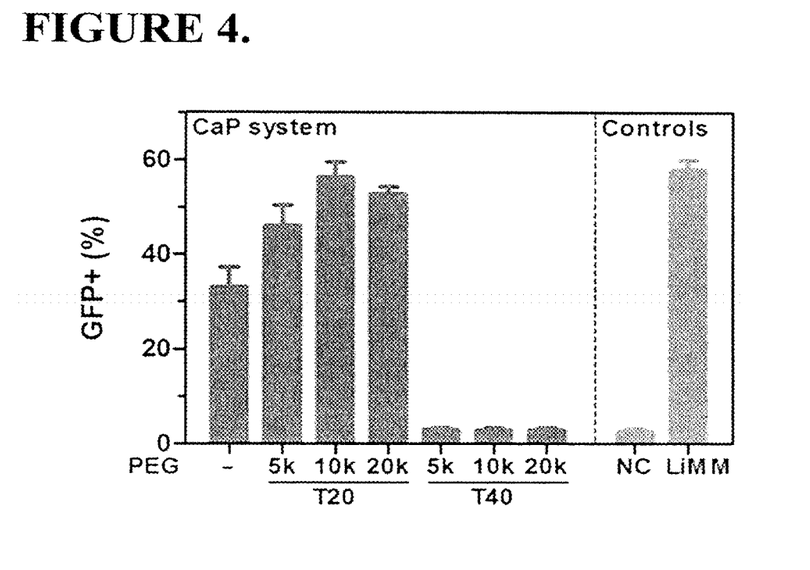
FIG. 4 shows the influence of the lengths of PEG and single-stranded DNA motif.

The influence of the lengths of PEG and single-stranded DNA motif in the performance of the DNA-templated micelle was studied as shown in FIG. 4. GFP (green fluorescent protein) mRNA (1 µg) was preloaded on a payload carrier, such as PEG5-T20 (PEG length at 5 kD and single-stranded DNA length at 20 nucleotides). Several payload carriers with the length of PEG in the range of 5-20 kD and the length of DNA at 20 or 40 nucleotides were used in this study, including PEG5-T20, PEG10-T20, PEG20-T20, PEG5-T40, PEG10-T40 and PEG20-T40.

The micelle was formed through nano-precipitation. THP1 cell was seeded in a 24-well plate in complete media without antibiotics at 4 hr prior to the transfection. Cells were treated with the micelles for 48 hr, and transfection efficiency with GFP expression in the live cell population was determined by FACS (fluorescence-activated cell sorting) with DAPI (4',6-diamidino-2-phenylindole) staining. Abbreviations in FIG. 4: NC, negative control; LiMM, Lipofectamine Messenger Max (available from Thermo Fisher Scientific).

Example 4. The Influence of the Lengths of mRNA Payloads

Figure 5:
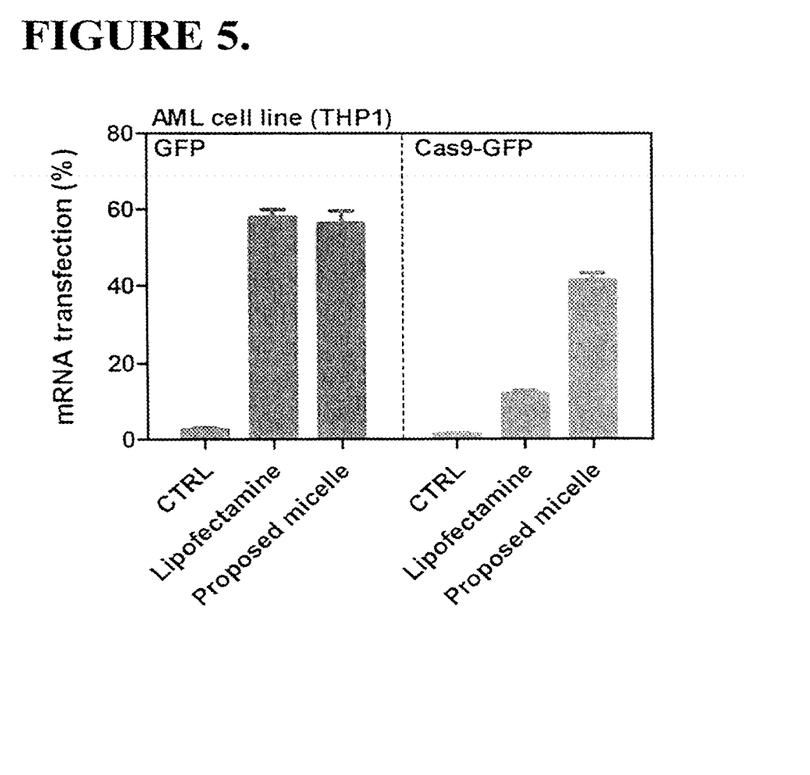
FIG. 5 shows the influence of the lengths of mRNA payloads.

THP1 cells were transfected with different mRNA payloads to study the influence of the lengths of mRNA payloads. GFP mRNA (1 mRNA length at approximately 996 nucleotides) or Cas9-GFP mRNA (1 μg, mRNA length at approximately 5,000 nucleotides) was preloaded on the payload carrier, PEG10-T20 (PEG at 101(D, DNA at 20 nucleotides). The micelle was formed through nano-precipitation. THP1 cell was seeded in a 24-well plate in complete media without antibiotics at 4 hr prior to the transfection. Cells were treated with the micelles for 48 hr, and transfection efficiency was determined by FACS with DAPI staining as shown in FIG. 5. Lipofectamine Messenger Max was used as a comparison (denoted as Lipofectamine in FIG. 5).

As shown in FIG. 5, for transfecting mRNA at approximately 996 nucleotides (GFP mRNA), the DNA-templated micelle containing PEG10-T20 payload carrier showed comparable transfection rate compared to Lipofectamine. For transfecting large mRNA at approximately 5,000 nucleotides (Cas9-GFP mRNA), the DNA-templated micelle containing PEG10-T20 payload carrier showed exceptional higher transfection rate compared to Lipofectamine (PEG10-T20 vs. Lipofectamine=40% vs. 10%).

Example 5. Particle Sizes of DNA-Templated Micelles

Figure 6:
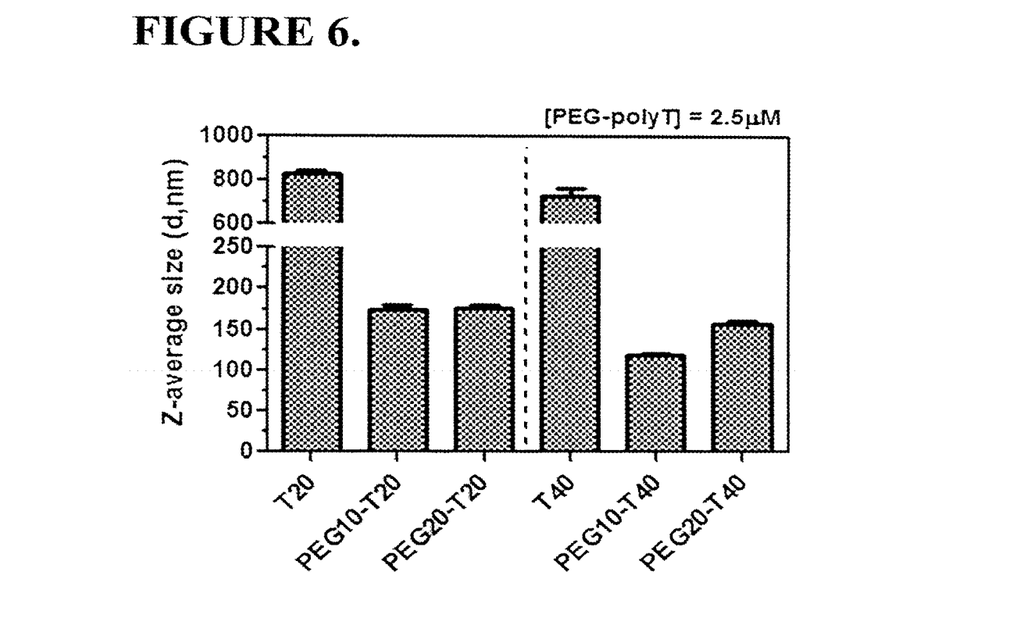
FIG. 6 shows the particle sizes of DNA-templated micelles.

Several DNA templates at the length of 20 or 40 nucleotides with or without PEG were used to form micelles, such as T20 (DNA at 20 nucleotides without PEG), or PEG10-T40 (DNA at 40 nucleotides with PEG at 10 kD). The DNA templates used in this study including T20, PEG10-T20, PEG20-T20, T40, PEG10-T40, and PEG20-T40. The micelles were formed through nano-precipitation. The sizes of the micelles were measured using Malvern ZetaSizer N590. In the presence of PEG, the micelles have the polydispersity (PDI) of less than 0.1 with the particle sizes in the range of 100-200 nm as shown in FIG. 6. The size of PEG-DNA and the presence of PEG were critical to control the formation of micelle in nano-sized with the polydispersity (PDI) of less than 0.1.

Example 6. The Influence of Ligand Density Using Large Protein Ligand

Figure 7:
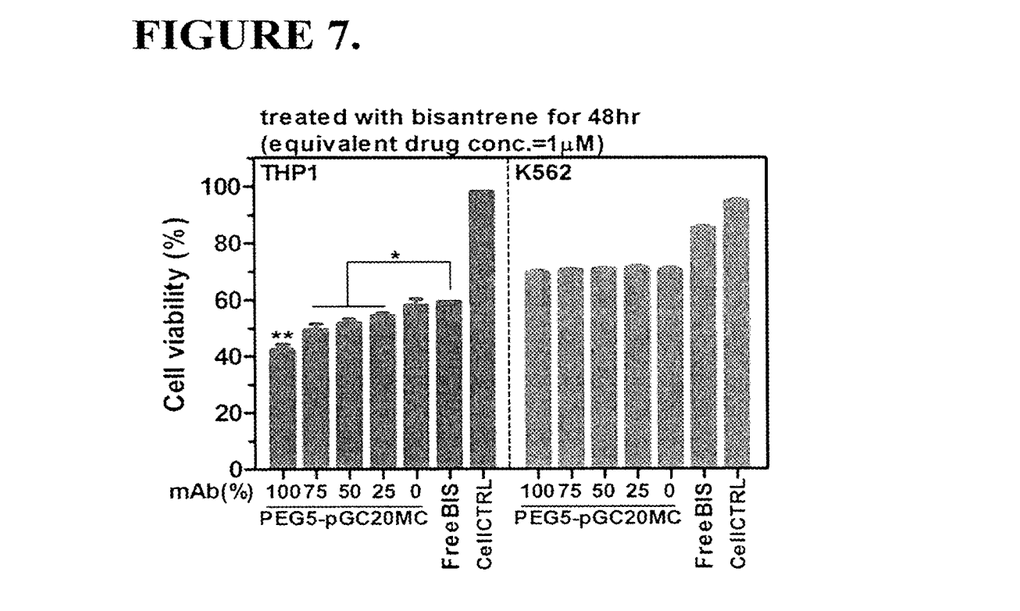
FIG. 7 shows the influence of ligand density using large protein ligand.

The ligand density is controllable in the formation of the DNA-templated micelles to achieve desired chemotherapy strategies. FIG. 7 shows the influence of ligand density, when large protein ligand, e.g. an antibody, was included in the DNA-templated micelle. Anti-IL1RAP antibody (denoted as mAb in FIG. 7) was used as a large protein ligand to be conjugated to PEG5-pGC20 payload carrier.

Two types of AML (Acute Myeloid Leukemia) cells, THP1 (high surface IL1RAP expression) and K562 (low surface IL1RAP expression), were seeded in a 96 well plate 4 hr prior to the treatment. Two types of PEG5-pGC20 payload carriers, with or without anti-IL1RAP, were mixed in a desired ratio to achieve various ligand densities in the range of 0 to 100% of anti-IL1RAP. 0% of anti-IL1RAP indicated the absence of anti-IL1RAP in the micelle. Bisantrene (BIS), a chemodrug to treat AML, was preloaded to the payload carriers prior to the formation of the micelles. Micelle were formed through nano-precipitation.

THP1 and K562 cells were treated with BIS (denoted as free BIS in FIG. 7, BIS without DNA-templated micelle) or micelle formulated BIS (denoted as PEG5-pGC20MC in FIG. 7) for 48 hr (equivalent BIS concentration=1 μM). Cell viability was determined by FACS with DAPI staining.

Example 7. Optimization of the Ligand Density Using a Small Chemical Ligand

Figure 8:
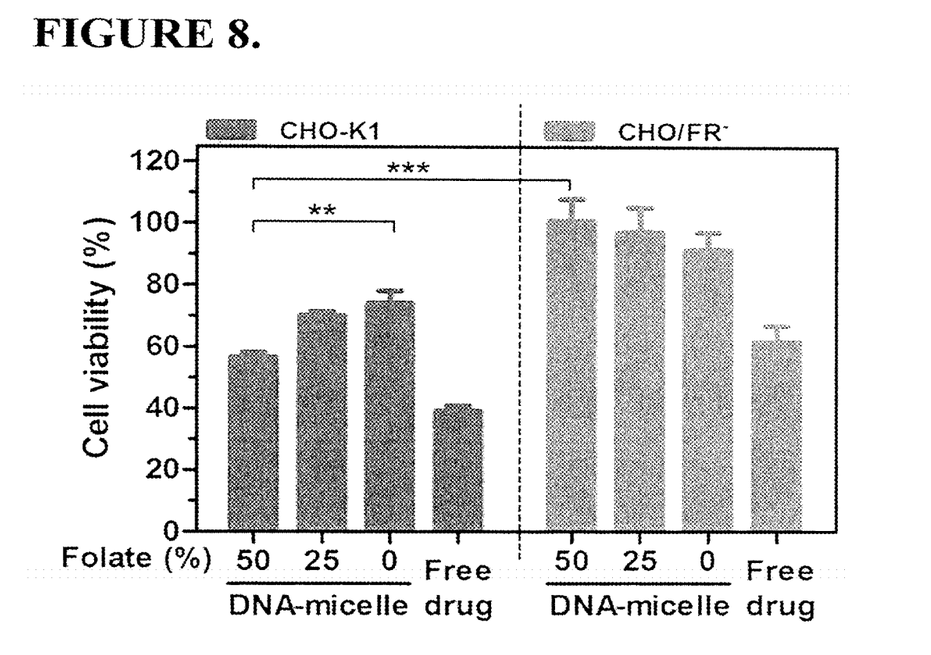
FIG. 8 shows controllable ligand density in the DNA-templated micelle for maximizing cellular uptake using a small chemical ligand.

FIG. 8 shows controllable ligand density in the DNA-templated micelle for maximizing cellular uptake using a small chemical ligand. A small chemical ligand, folate, was used to optimize the delivery of a chemodrug, mitoxantrone (MTX, Sigma-Aldrich M6545), through folate-conjugated DNA-templated micelle. Folate was used as a small chemical ligand to be conjugated to PEG20-T40 payload carrier.

Two types of CHO cells, CHO-K1 (wild-type, folate receptor expressed) and CHO/FR (folate receptor deficient), were seeded in a 96 well plate one day prior to the treatment. Two types of PEG20-T40 payload carriers, with or without folate, were mixed in a desired ratio to achieve various ligand densities in the range of 0 to 50% of folate. 0% of folate indicated the absence of folate in the micelle. Mitoxantrone (MTX), was preloaded to the payload carriers prior to the formation of the micelles. Micelle were formed through nano-precipitation.

The CHO-K1 and CHO/FR cells were treated with free MTX (MTX without micelle) or micelle-formulated MTX for 24 hr (equivalent MTX concentration=1.5 μM). Cell viability was determined by MTS assay. The efficacy of delivering MTX was enhanced by optimizing the ligand (folate) density as shown in FIG. 8. The controllable ligand density in the DNA-templated micelle demonstrated the feasibility of maximizing cellular uptake.

Example 8. Micelle Stability Study

Figure 9:
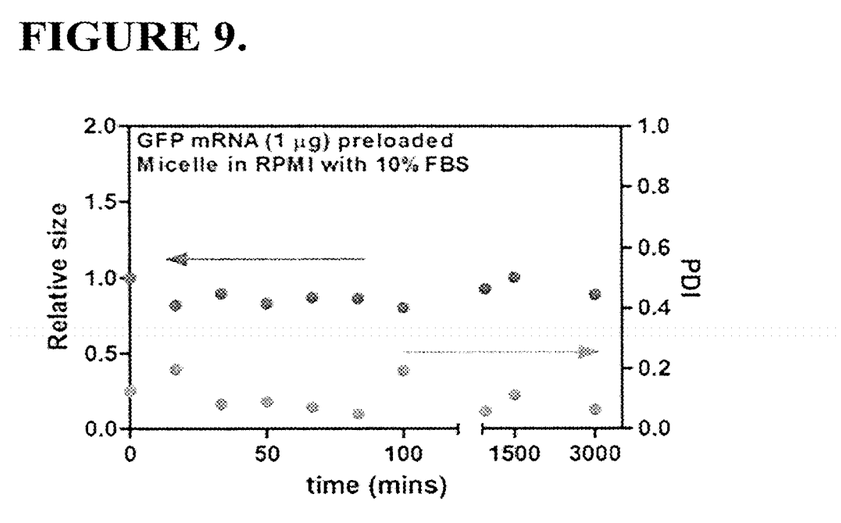
FIG. 9 shows the results of micelle stability study.

FIG. 9 shows the results of micelle stability study. PEG20-T40 payload carrier was conjugated with folate and preloaded with GFP mRNA (1 μg). The micelles were formed through nano-precipitation and subsequently incubated with 450 μL of complete media (RPMI1640 with 10% FBS). The size of the micelle was measured using Malvern ZetaSizer NS90 in a time course. The result at each time point was normalized to that at time=0. The micelle held a z-average diameter of 141.8±10.18 nm at time=0.

Example 9. Cytotoxicity Study

Figure 10:
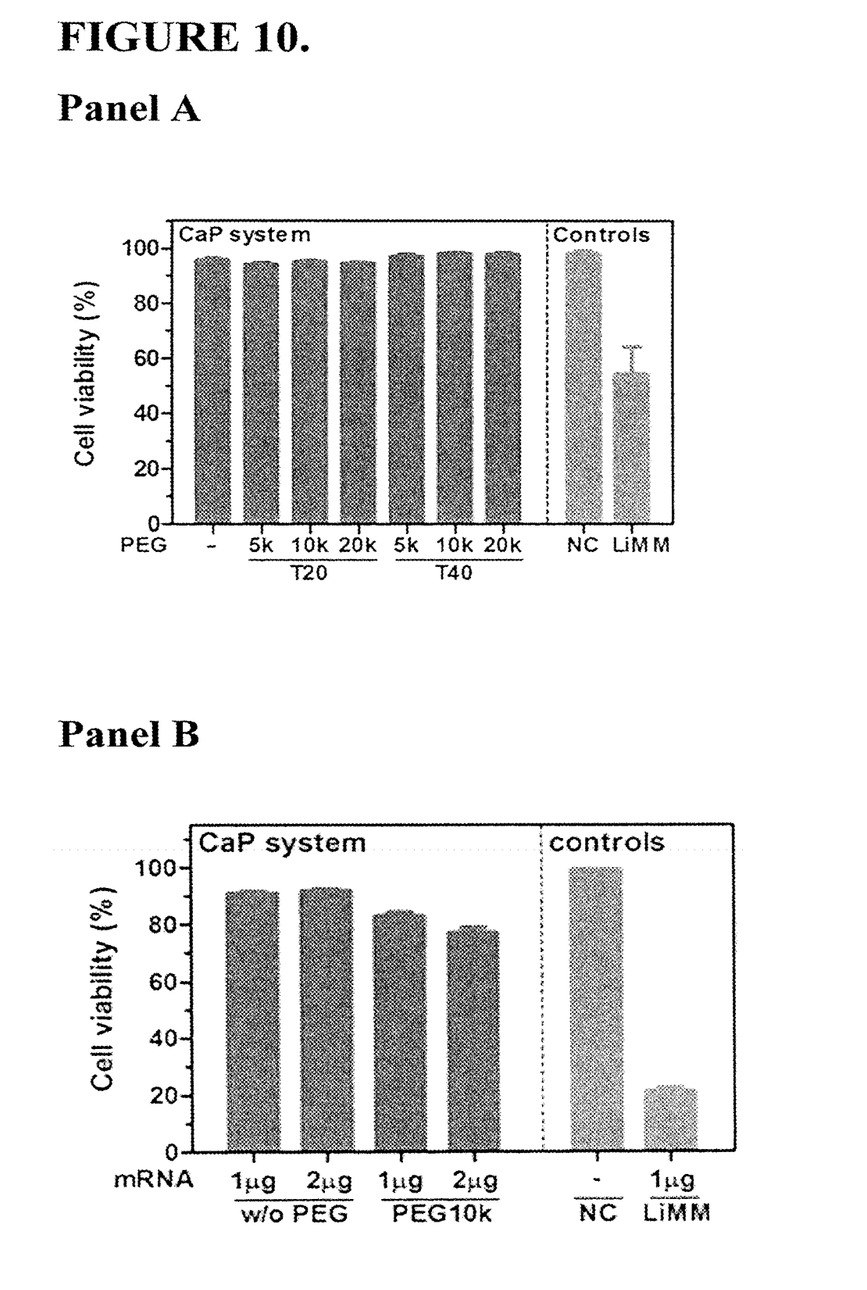
FIG. 10 shows the results of cytotoxicity study of the DNA template micelles.

FIG. 10 shows the results of cytotoxicity study of the DNA template micelles. As shown in FIG. 10, panel A indicates GFP mRNA transfection, panel B indicates Cas9-GFP mRNA transfection. GFP mRNA or Cas9-GFP mRNA (1 μg each) was preloaded on the payload carrier. The micelles were formed through nano-precipitation. THP1 cell was seeded in a 24-well plate in complete media without antibiotics at 4 hr prior to the transfection. Cells were treated with the micelles for 48 hr, and the cell viability was determined by FACS with DAPI staining. Abbreviations in FIG. 10: NC, negative control; LiMM, Lipofectamine Messenger Max.

Example 10. Transfection on Adherent Cells

Figure 11:
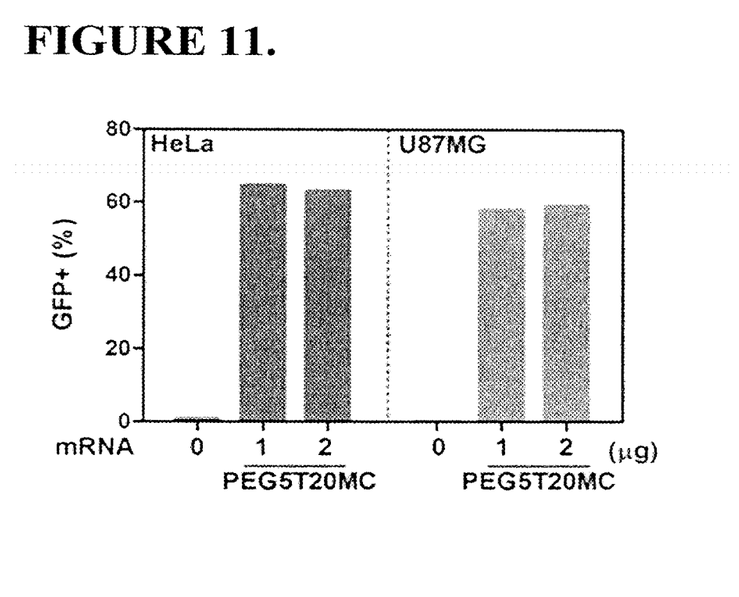
FIG. 11 shows the application of DNA-templated micelles in transfecting adherent cells.

FIG. 11 shows the application of DNA-templated micelles in transfecting adherent cells, HeLa and U87MG cells. GFP mRNA (1 or 2 μg) was preloaded on payload carrier (PEG5-T20). Micelles were formed through nano-precipitation. HeLa and U87MG cells were seeded in a 24-well plate in complete media one day prior to the transfection. Cells were treated with the micelles for 24 hr, and transfection efficiency of GFP in the live cell population was determined as shown in FIG. 11.

Example 11. Application of the Multifunctional DNA-Templated Micelles in Specifically Delivering Drugs to Brain Tumors In order to reduce undesirable uptake of the DNA-templated micelles by normal cells, the DNA bridge of the payload carrier was conjugated with a long amine-functionalized PEG segment with a molecular weight of 20 kD, and the amine-functionalized PEG segment was conjugated with a targeting peptide, Pep1, which recognizes interleukin 13 receptor alpha 2 (IL13RA2). 25% of the amino-groups on the surfaces of the DNA-templated micelles were replaced by Pep1. For drug loading, mitoxantrone was preloaded onto the payload carrier through intercalation through a gradient-annealing process from 94° C. to 4° C. with a cooling rate at −1° C./sec. The Pep1-modified and mitoxantrone-loaded DNA-templated micelle was tested on different types of brain tumor cells with low, medium and high expression of IL13RA2, respectively. The results showed that this Pep1-modified and mitoxantrone-loaded DNA-templated micelle specifically killed the IL13RA2-expressed tumor cells.

Example 12. DNA-Templated Micelle/MSC Cluster for Glioblastoma Therapeutics

Figure 12:
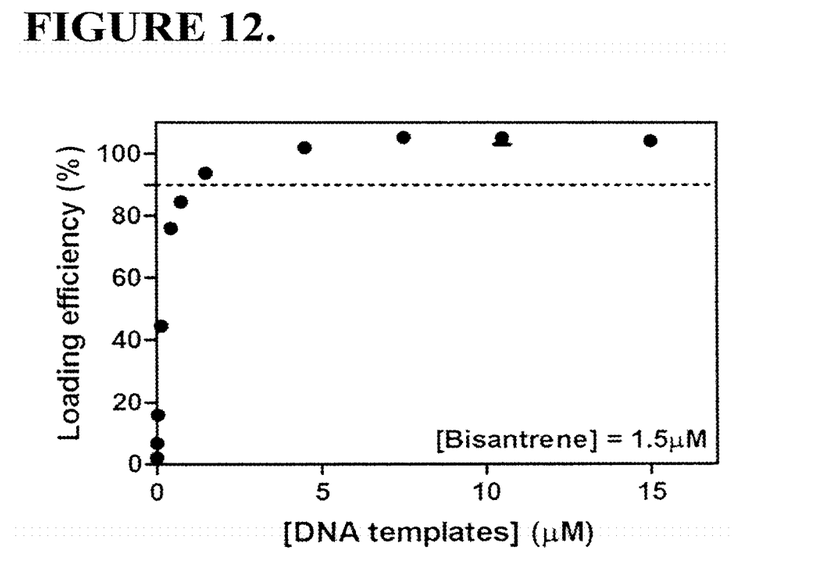
FIG. 12 shows size tunable, highly stable DNA-templated micelles with high drug loading efficiency.

Payload carriers were purified by reversed-phased HPLC using an acetonitrile/PBS (phosphate-buffered saline) mixture as an eluent. The therapeutic payloads (such as chemodrugs and polynucleotides) were loaded onto the payload carrier through a gradient annealing process with a cooling rate of −1° C./min. Payload-carrying DNA-templated micelles were formed via nano-precipitation. The formulation of forming this DNA-templated micelle was optimized for simultaneously loading of drug and nucleic acid. The size of the loaded DNA-templated micelles was tunable and ranged from 15 nm to 150 nm with a narrow polydispersity (PDI<0.1). The micelles were colloidally stable in serum-containing environment. FIG. 12 shows size tunable, highly stable DNA-templated micelles with high drug loading capacity. As shown in FIG. 12, the loading efficiency reached nearly 100%.

To decorate a mesenchymal stem cell (MSC) cluster with DNA-templated micelles, DNA-templated micelles were mixed with an alginate-containing MSC suspension at the ratio of 1:1, and the micelle-MSC clusters were subsequently formed via a microfluidic technology.

To enhance the therapeutic efficacy in glioblastoma (GBM) treatment, a micelle-MSC hybrid cluster was developed for co-delivering multiple anti-cancer drugs. MSCs hold tumor homing property as they express tumor-associated cytokine receptors. MSCs in the cluster form showed higher migration toward GBM cells. In micelle-MSC clusters, more than 50% of the DNA-templated micelles were loaded on the extracellular matrix of the micelle-MSC cluster and were not internalized by the MSCs. In addition, MSC migration was not affected by the decoration of DNA-templated micelles. These DNA-templated micelles were size-tunable, colloidally stable, relatively monodispersed and low toxic, which can be integrated synergistically with other anti-cancer approaches to improve the efficacy in cancer therapy.

Figure 13:
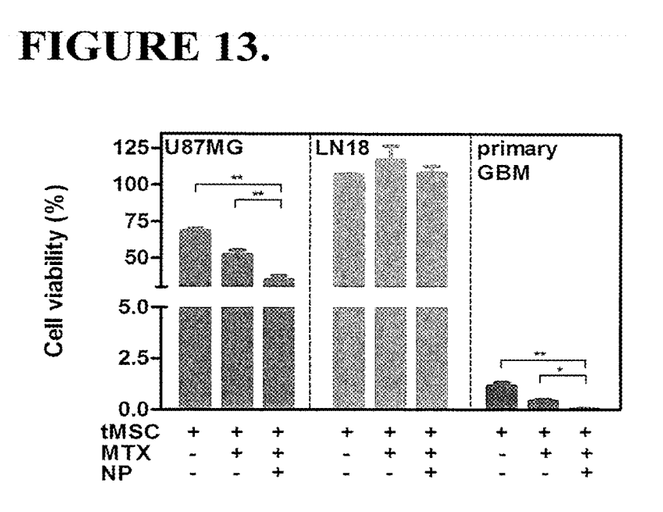
FIG. 13 shows specific glioblastoma (GBM) cell killing using DNA-templated micelle/MSC hybrid cluster.

FIG. 13 shows specific glioblastoma (GBM) cell killing using DNA-templated micelle/MSC hybrid cluster. The targeted, drug-preloaded micelle was formed with Pep1-conjugated DNA template (25% coverage) and mitoxantrone (MTX, Sigma-Aldrich M6545). Subsequently the micelle/MSC hybrid cluster, free MTX/MSC cluster or MSC cluster was formed. Three GBM cells, LN18 (Pep1-receptor deficient), U87MG (high Pep1-receptor expression) and primary GBM cells, were co-cultured with the clusters. Cell viability of the GBM cell was determined using the Promoga Cell-Titer-Glo Luminescent Cell Viability Assay kit. Abbreviations in FIG. 13: MSC, mesenchymal stem cell; MTX, mitoxantrone; NP, nanoparticle, e.g. DNA-templated micelle; GBM, glioblastoma.

Example 13. Application of DNA-Templated Micelles in Transfecting Cells with mRNAs and Small Nucleic Acids The DNA bridge of the payload carrier was designed as a partial complement to a polynucleotide (as a payload of the DNA bridge of the payload carrier) with a 37° C. melting temperature. Micelles containing this payload carrier was tested in a wide spectrum of cell lines, including adherent cells, such as HeLa and U87MG cells, and suspension cells, such as THP-1 cell. This payload carrier was used to deliver green fluorescent protein (GFP) mRNA to these cells with 50-70% transfection efficiency which was comparable to the commercially-available transfection reagent, Lipofectamine Messenger Max (available from Thermo Fisher Scientific). However, the micelle containing this payload carrier resulted in less cytotoxicity to the cells at <10% compared to Lipofectamine at 50-70%. This payload carrier also was used to transfect the hard-to-transfect cell line, THP1, with a long mRNA, such as Cas9 mRNA for CRISPR/Cas9 genome editing system, at 40% efficiency, whereas Lipofectamine reached only 5-10% efficiency with the same long mRNA. Co-delivery of Cas9 mRNA and its guide RNA (gRNA) of the CRISPR/Cas9 genome editing system was also validated in a cellular uptake assay, which showed that 98-99% of the Cas9 mRNA and gRNA co-localized inside the transfected cells.

Example 14. Application of the Multifunctional DNA-Templated Micelle for Leukemia Immunotherapy Two types of payload carriers were designed. One type was conjugated with an antibody that recognizes a leukemic stem cell biomarker, and the other type was conjugated with human Fc protein that can recruit immune cells, including natural killer (NK) cells and macrophage. The payload carrier was loaded with a chemodrug, bisantrene. The modified and loaded DNA-templated micelle was found to not only specifically kill cancer cells, but also was able to induce phagocytosis of immune cells.

The term "about" as used herein means that the value is not necessarily precise and could vary by ±10% or even ±5%.

It is to be understood that the present invention is not to be limited to the exact description and embodiments as illustrated and described herein. To those of ordinary skill in the art, one or more variations and modifications will be understood to be contemplated from the present disclosure. Accordingly, all expedient modifications readily attainable by one of ordinary skill in the art from the disclosure set forth herein, or by routine experimentation therefrom, are deemed to be within the true spirit and scope of the invention as defined by the appended claims.

What is claimed is:

1. A micelle system for delivering at least one payload to cells, the micelle system comprising at least one payload carrier, wherein the payload carrier comprises at least one DNA bridge and at least one functionalized polyethylene glycol (PEG) segment, wherein the functionalized PEG segment is covalently bound to the DNA bridge, wherein the DNA bridge compromises a single-stranded DNA and serves as a delivery vehicle for at least one payload through intercalation or nucleotide base pairing.

2. The micelle system of claim 1, wherein the functionalized PEG segment is further conjugated to at least one ligand.

3. The micelle system of claim 2, wherein a density of the ligand of the micelle system is controllable in the range of from 0% to 100%.

4. The micelle system of claim 1, wherein the payload carrier is preloaded with at least one payload prior to the formation of micelle.

5. The micelle system of claim 1, wherein the payload carrier is further conjugated with at least one ligand prior to the formation of micelle.

6. The micelle system of claim 1, wherein the functionalized PEG segment is an amine-functionalized PEG segment.

7. The micelle system of claim 1, wherein the DNA bridge is a single-stranded DNA in the range of from about 8 nucleotides to about 100 nucleotides.

8. The micelle system of claim 1, wherein the payload is a small molecule, compound, drug, chemodrug, polynucleotide, DNA, gene, messenger RNA (mRNA), aptamer, or a combination thereof.

9. The micelle system of claim 2, wherein the ligand is a small molecule, peptide, antibody, aptamer, polynucleotide, or a combination thereof.

10. The micelle system of claim 1, wherein the size of the micelle is from about 5 nm to about 250 nm.

11. The micelle system of claim 1, wherein the molecular weight of the PEG segment is in the range of from about 1 kD to about 30 kD.

12. The micelle system of claim 1, wherein the polydispersity of the micelle is less than about 0.1.

13. A method for delivering a payload to cells of a subject for disease treatment, comprising administering to the subject a pharmaceutical composition comprising the micelle system of claim 1.

14. The method of claim 13, wherein the disease treatment is cell transfections, gene therapy, chemotherapy, immunotherapy, cancer treatment, disease monitoring, brain tumor chemotherapy, glioblastoma chemotherapy, or leukemia immunotherapy.

15. A kit for performing a cell transfection reaction, comprising the micelle system of claim 1.

* * * * *

UNITED STATES PATENT AND TRADEMARK OFFICE
CERTIFICATE OF CORRECTION

| | |
|---|---|
| PATENT NO. | : 11,311,629 B2 |
| APPLICATION NO. | : 16/492320 |
| DATED | : April 26, 2022 |
| INVENTOR(S) | : Kam W. Leong et al. |

It is certified that error appears in the above-identified patent and that said Letters Patent is hereby corrected as shown below:

In the Claims

Claim 1 at Column 11, Line 11: "compromises" should read --comprises--.

Signed and Sealed this
Second Day of January, 2024

Katherine Kelly Vidal
Director of the United States Patent and Trademark Office